United States Patent
Sinha et al.

(10) Patent No.: US 10,068,333 B2
(45) Date of Patent: Sep. 4, 2018

(54) SYSTEMS AND METHODS FOR IDENTIFYING BODY JOINT LOCATIONS BASED ON SENSOR DATA ANALYSIS

(71) Applicant: Tata Consultancy Services Limited, Mumbai (IN)

(72) Inventors: Sanjana Sinha, Kolkata (IN); Brojeshwar Bhowmick, Kolkata (IN); Kingshuk Chakravarty, Kolkata (IN); Aniruddha Sinha, Kolkata (IN); Abhijit Das, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 15/466,676

(22) Filed: Mar. 22, 2017

(65) Prior Publication Data

US 2018/0047157 A1 Feb. 15, 2018

(30) Foreign Application Priority Data

Aug. 10, 2016 (IN) .............................. 201621027388

(51) Int. Cl.
*G06T 7/00* (2017.01)
*G06T 7/143* (2017.01)
(Continued)

(52) U.S. Cl.
CPC .......... *G06T 7/0012* (2013.01); *A61B 5/1121* (2013.01); *A61B 5/1128* (2013.01);
(Continued)

(58) Field of Classification Search
CPC ......... G06T 7/0012; G06T 7/143; G06T 7/75; G06T 7/593; G06T 7/70; G06T 7/0083;
(Continued)

(56) References Cited

U.S. PATENT DOCUMENTS 8,073,521 B2 * 12/2011 Liew et al. .............. A61B 5/00
600/407
2014/0035805 A1 2/2014 Minnen et al.

FOREIGN PATENT DOCUMENTS

| CN | 103473571 A | 12/2013 |
| CN | 104598890 A | 5/2015 |

(Continued)

OTHER PUBLICATIONS

Han, J. et al, "Enhanced Computer Vision with Microsoft Kinect Sensor: A Review", IEEE Transactions on Cybernetics, vol. 43, No. 5, pp. 1318-1334, (2013)

*Primary Examiner* — Duy M Dang
(74) *Attorney, Agent, or Firm* — Finnegan, Henderson, Farabow, Garrett & Dunner LLP

(57) ABSTRACT

Systems and methods for identifying body joint location includes obtaining skeletal data, depth data and red, green, and blue (RGB) data pertaining to a user, obtaining, using input data, an estimate of body joint locations (BJLs) and body segment lengths (BSLs), iteratively identifying, based on the depth data and RGB data, probable correct BJLs in a bounded neighborhood around BJLs that are previously obtained, comparing a body segment length associated with the probable correct BJLs and a reference length, identifying candidate BJLs based on comparison, determining a physical orientation of each body segment by segmenting three dimensional (3D) coordinates of each body segment based on the depth data and performing an analysis on each segmented 3D coordinate. A corrected BJL is identified based on a minimal deviation in direction from the physical orientation of a corresponding body segment along with a feature descriptor of the RGB data and depth data.

15 Claims, 6 Drawing Sheets

(51) Int. Cl.
*G06T 7/593* (2017.01)
*G06T 7/70* (2017.01)
*A61B 5/00* (2006.01)
*A61B 5/11* (2006.01)
*G06T 7/73* (2017.01)

(52) U.S. Cl.
CPC ............ *A61B 5/7271* (2013.01); *G06T 7/143* (2017.01); *G06T 7/593* (2017.01); *G06T 7/70* (2017.01); *G06T 7/75* (2017.01); *G06T 2207/10016* (2013.01); *G06T 2207/10024* (2013.01); *G06T 2207/10028* (2013.01); *G06T 2207/30008* (2013.01); *G06T 2207/30241* (2013.01)

(58) Field of Classification Search
CPC ........... G06T 2207/3004; G06T 7/0081; G06T 2207/10081; G06T 11/006; G06T 2207/10116; G06T 2207/30004; G06T 5/40; G06T 2207/30068; G06T 7/0085; G06T 7/60; G06T 1/20; G06T 17/20; G06T 1/60; G06T 5/742; A61B 5/1121; A61B 5/1128; A61B 5/7271; A61B 6/032; A61B 5/02007; A61B 5/7264; A61B 7/0012; G06F 19/321; G06F 17/5018; G06F 9/5044; G06F 2217/16; G06K 9/4604; G06K 9/52; G06K 9/6267; G06K 9/66

See application file for complete search history.

(56) References Cited

FOREIGN PATENT DOCUMENTS

DE 102014013828 A1 3/2016
WO WO 2015162158 A1 10/2015

\* cited by examiner

| ROM exercise | Length over time | | Mean (meter) | Standard Deviation (meter) | Range (max-min) (meter) | Coefficient of variation | % Improvement |
|---|---|---|---|---|---|---|---|
| Shoulder Abduction-Adduction | Arm | Kinect | 0.2713 | 0.0197 | 0.0806 | 0.0724 | 73.8 |
| | | Corrected | 0.2676 | 0.0051 | 0.032 | 0.0189 | |
| | Forearm | Kinect | 0.2488 | 0.0223 | 0.0862 | 0.0897 | 74.3 |
| | | Corrected | 0.2319 | 0.0053 | 0.039 | 0.023 | |
| Shoulder Flexion-Extension | Arm | Kinect | 0.2707 | 0.0171 | 0.0757 | 0.0632 | 72.9 |
| | | Corrected | 0.269 | 0.0046 | 0.0309 | 0.0171 | |
| | Forearm | Kinect | 0.2524 | 0.02176 | 0.0876 | 0.0863 | 80.7 |
| | | Corrected | 0.3261 | 0.0054 | 0.033 | 0.0166 | |
| Elbow Flexion-Extension | Arm | Kinect | 0.2435 | 0.0189 | 0.0544 | 0.0777 | 71.6 |
| | | Corrected | 0.2528 | 0.0056 | 0.0219 | 0.022 | |
| | Forearm | Kinect | 0.2354 | 0.0143 | 0.0792 | 0.0545 | 58.7 |
| | | Corrected | 0.2289 | 0.00516 | 0.0333 | 0.02254 | |

FIG. 3

(a) for shoulder abduction (b) for elbow flexion

US 10,068,333 B2

SYSTEMS AND METHODS FOR IDENTIFYING BODY JOINT LOCATIONS BASED ON SENSOR DATA ANALYSIS

PRIORITY CLAIM

This U.S. patent application claims priority under 35 U.S.C. § 119 to: India Application No. 201621027388, filed on Aug. 10, 2016. The entire contents of the aforementioned application are incorporated herein by reference.

TECHNICAL FIELD

This disclosure relates generally to sensor data analysis, and more particularly to systems and methods for identifying body joint locations based on sensor data analysis.

BACKGROUND

Joint motion analysis is an important aspect of health monitoring/rehabilitation of patients suffering from neurological disorders, post stroke patients, and elderly subjects. Joint movement data capture is traditionally done using clinical devices such as Vicon, which is marker-based and extremely expensive and ill-suited for prolonged rehabilitation therapy. Kinect® is a marker-less motion capture device that is being used for its low cost, portability and ease of cost when compared to its expensive counterpart. The accuracy of Kinect® as an alternative to Marker-based systems has been widely studied and there are extensive reports on its validity and reliability in comparison to Vicon. However, the reports indicate a lower accuracy of the human body joint information provided by Kinect® skeletal data. The skeleton data provided by Kinect® requires further optimization to improve its accuracy and allow effective and reliable assessment.

SUMMARY

Embodiments of the present disclosure present technological improvements as solutions to one or more of the above-mentioned technical problems recognized by the inventors in conventional systems. For example, in an aspect, a hardware processor implemented method for identifying body joint locations is provided. The method comprises obtaining, by one or more hardware processors, input data comprising skeletal data, depth data, and red, green, and blue (RGB) data pertaining to at least one user at one or more time stamps, wherein the one or more input data comprises three dimensional (3D) coordinates pertaining to one or more skeleton joints. The method further comprises estimating, using the one or more input data, by the one or more hardware processors, one or more body joint locations and a body segment length of one or more body segments connected to corresponding skeleton joints to obtain (i) an estimate of one or more body joint locations and (ii) an estimate of one or more body segment lengths. In an embodiment, the one or more body segment lengths are based on a Euclidean distance between adjacent skeleton joints. One or more probable correct body joint locations are identified in a bounded neighborhood around the one or more body joint locations that are previously obtained in a previous frame, wherein the one or more probable correct body joint locations are iteratively identified based on the depth data and the RGB data. In an example embodiment, a search region is defined for identifying the one or more probable correct body joint locations using a radius equivalent to a displacement of a corresponding skeleton joint in a single frame. The method further comprises performing, by the one or more hardware processors, a comparison of (i) a body segment length associated with each of the one or more probable correct body joint locations and (ii) a reference length. In an embodiment, the reference length is derived based on the estimate of the one or more body segment lengths. A subset of the one or more probable correct body joint locations are identified as one or more candidate body joint locations based on the comparison. In an embodiment, the subset of the one or more probable correct body joint locations are identified as one or more candidate body joint locations based on the comparison resulting in a minimal body segment length variation. A physical orientation of each body segment pertaining to each of the one or more candidate body joint locations is determined by segmenting one or more 3D coordinates of each body segment based on the depth data and performing an analysis on each segmented 3D coordinate. A (corrected) body joint location is identified from the one or more candidate body joint locations based on a minimal deviation in direction from the physical orientation of a corresponding body segment along with a feature descriptor of the RGB data and the depth data, wherein the minimal deviation is based on the depth data, and, wherein the minimal deviation is based on one or more actions performed by the user.

In another aspect, a system for identifying a body joint location is provided. The system comprises a memory storing instructions, one or more communication interfaces, and one or more hardware processors coupled to the memory using the one or more communication interfaces, wherein the one or more hardware processors are configured by the instructions to: obtain one or more input data comprising skeletal data, depth data and red, green, and blue (RGB) data pertaining to at least one user at one or more time stamps, wherein the one or more input data comprising three dimensional (3D) coordinates pertaining to one or more skeleton joints. The skeletal data, depth data and red, green, and blue (RGB) data are captured by a sensor (e.g., Kinect® sensor). The one or more hardware processors are further configured by the instructions to estimate, using the one or more input data, one or more body joint locations and a body segment length of one or more body segments connecting to corresponding skeleton joints to obtain (i) an estimate of one or more body joint locations and (ii) an estimate of one or more body segment lengths. In an embodiment, one or more body segment lengths are based on a Euclidean distance between adjacent skeleton joints. In an embodiment, the system is further configured to identify one or more probable correct body joint locations in a bounded neighborhood around the one or more body joint locations that are previously obtained from a previous frame, wherein the one or more probable correct body joint locations are iteratively identified based on the depth data and the RGB data. In an embodiment, a search region is defined to identify the one or more probable correct body joint locations based on a radius equivalent to a displacement of a corresponding skeleton joint in a single frame.

The system further performs a comparison of (i) a body segment length associated with each of the one or more probable correct body joint locations and (ii) a reference length. In an embodiment, the reference length is derived based on the estimate of the one or more body segment lengths. The system further identifies a subset of the one or more probable correct body joint locations as one or more candidate body joint locations based on the comparison. In an embodiment, the subset of the one or more probable correct body joint locations are identified as one or more candidate body joint locations based on the comparison resulting in a minimal body segment length variation. In other words, probable correct body joint locations having a minimal body segment length variation with respect to the reference length are identified as one or more candidate body joint locations.

The system is further configured to determine a physical orientation of each body segment pertaining to each of the one or more candidate body joint locations by segmenting one or more 3D coordinates of each body segment based on the depth data and performing an analysis on each segmented 3D coordinate. The system is further configured to identify, from the one or more candidate body joint locations, a (corrected) body joint location based on a minimal deviation in direction from the physical orientation of a corresponding body segment along with a feature descriptor of the RGB data and the depth data, wherein the minimal deviation is based on the depth data, and wherein the minimal deviation is based on one or more actions performed by the user. In an embodiment, a body joint location having a minimal deviation in direction from the physical orientation of a corresponding body segment is identified as a corrected joint body location along with a feature descriptor of the RGB data and the depth data.

In yet another aspect, one or more non-transitory machine readable information storage mediums comprising one or more instructions is provided. The one or more instructions which when executed by one or more hardware processors causes obtaining input data comprising skeletal data, depth data and red, green, and blue (RGB) data pertaining to at least one user at one or more time stamps, wherein the input data comprises three dimensional (3D) coordinates pertaining to one or more skeleton joints. The one or more instructions which when executed by one or more hardware processors further causes estimating, using the one or more input data, one or more body joint locations and a body segment length of one or more body segments connecting to corresponding skeleton joints to obtain (i) an estimate of one or more body joint locations and (ii) an estimate of one or more body segment lengths. In an embodiment, the one or more body segment lengths are based on a Euclidean distance between adjacent skeleton joints. The one or more instructions which when executed by one or more hardware processors causes identifying one or more probable correct body joint locations in a bounded neighborhood around the one or more body joint locations that are previously obtained, wherein the one or more probable correct body joint locations are iteratively identified based on the depth data and the RGB data. In an example embodiment, a search region is defined for identifying the one or more probable correct body joint locations using a radius equivalent to a displacement of a corresponding skeleton joint. The one or more instructions which when executed by one or more hardware processors further causes performing a comparison of (i) a body segment length associated with each of the one or more probable correct body joint locations and (ii) a reference length. In an embodiment, the reference length is derived based on the estimate of the one or more estimated body segment lengths. The one or more instructions which when executed by one or more hardware processors further causes identifying a subset of the one or more probable correct body joint locations as one or more candidate body joint locations based on the comparison. In an embodiment, identifying a subset of the one or more probable correct body joint locations as one or more candidate body joint locations is based on the comparison resulting in a minimal body segment length variation. The one or more instructions which when executed by one or more hardware processors further causes determining a physical orientation of each body segment pertaining to each of the one or more candidate body joint locations by segmenting one or more 3D coordinates of each body segment based on the depth data and performing an analysis on each segmented 3D coordinate. The one or more instructions which when executed by one or more hardware processors further causes identifying, from the one or more candidate body joint locations, a (corrected) body joint location based on a minimal deviation in direction from the physical orientation of a corresponding body segment along with a feature descriptor of the RGB data and the depth data, wherein said minimal deviation is based on the depth data, and, wherein the minimal deviation is based on one or more actions performed by the user.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 3 illustrates an exemplary table indicating body segment length statistics for ROM exercises for 10 subjects, according to an embodiment of the present disclosure.

DETAILED DESCRIPTION

Figure 1:
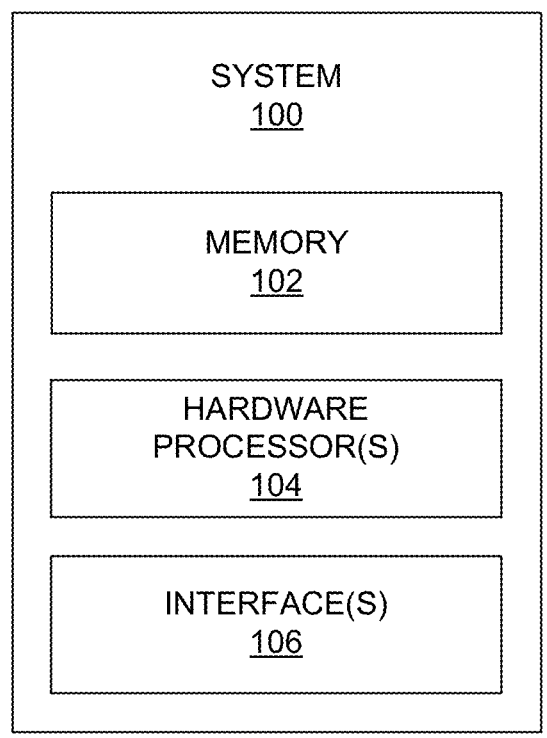
FIG. 1 illustrates an exemplary block diagram of a system for identifying a body joint location of a user in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Body joint movement analysis is extremely essential for health monitoring and treatment of patients with neurological disorders and stroke. Chronic hemiparesis of the upper extremity following a stroke causes major hand movement limitations. There is possibility of permanent reduction in muscle co-activation and corresponding joint torque patterns due to stroke. Several studies suggest that abnormal coupling of shoulder abductors with elbow flexors, and shoulder adductors with elbow extensors often leads to some stereotypical movement characteristics exhibited by severe stroke patients. Therefore continuous and effective rehabilitation therapy is absolutely essential to monitor and control such abnormalities. There is a substantial need for home-based rehabilitation post-clinical therapy.

Marker-based systems for human body motion capture and analysis, (such as Vicon) are popular in upper extremity rehabilitation for their clinically approved levels of accuracy. But marker less systems for motion capture, such as Microsoft Kinect®, are feasible for home-based rehabilitation due to their affordability and portability. The accuracy, validity and test-retest reliability measures of Kinect have been studied for range of motion, postural control and gait. The results reported indicate a disparity between body joint locations observed by Kinect and that obtained by a clinical gold standard stereophotogrammetry system such as Vicon. Body segment length variations of the order of 6-8 centimeters (cms) for arm, and 2-5 cms for forearm were reported while using Kinect® as it provides a non-anthropometric skeleton model. Moreover the error was found to be lower for upper body than lower body joints. The performance of Kinect® has also been studied for non-healthy subjects and elderly population Experimental results showed that the accuracy of Kinect® for measuring gross spatial movement, such as shoulder and elbow movement, was higher than that for fine movements (such as hands). The disparity in body semantics such as body segment length and orientation increases during movement. It is therefore essential to improve accuracy of Kinect® in measurements related to clinical assessment and biomechanical modeling. For example, accurate measurement of arm length is important for assessing performance of reaching task for patients with impairments in the paretic arm. Prior work has been done on categorizing patients from movement pattern using only bone length derived from Kinect® skeleton data. Some had explicitly mentioned the need of further optimization of joint positions and body segment length using additional depth information from Kinect®.

The embodiments of the present disclosure aims at improving accuracy of Kinect® in rehabilitation for upper extremities such as shoulder and elbow joints by improving joint center localization using additional Depth and RGB (RGBD) data, with constraints on body segment length and orientation. More particularly, the embodiments of the present disclosure implement systems and methods for sensor data analysis based identification of a body joint location that enables minimizing temporal variation in body segment length based on RGB and depth information obtained from Kinect® sensor, aligns connected joint pairs in the direction of physical body segment orientation using Depth-based segmentation and analysis (e.g., Principal Component Analysis (PCA)) on segmented 3D coordinates, and provides reliable range of motion analysis system based on corrected joint information.

Referring now to the drawings, and more particularly to FIGS. 1 through 7, where similar reference characters denote corresponding features consistently throughout the figures, there are shown preferred embodiments and these embodiments are described in the context of the following exemplary system and/or method.

FIG. 1 illustrates an exemplary block diagram of a system 100 for identifying a body joint location of a user in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2:
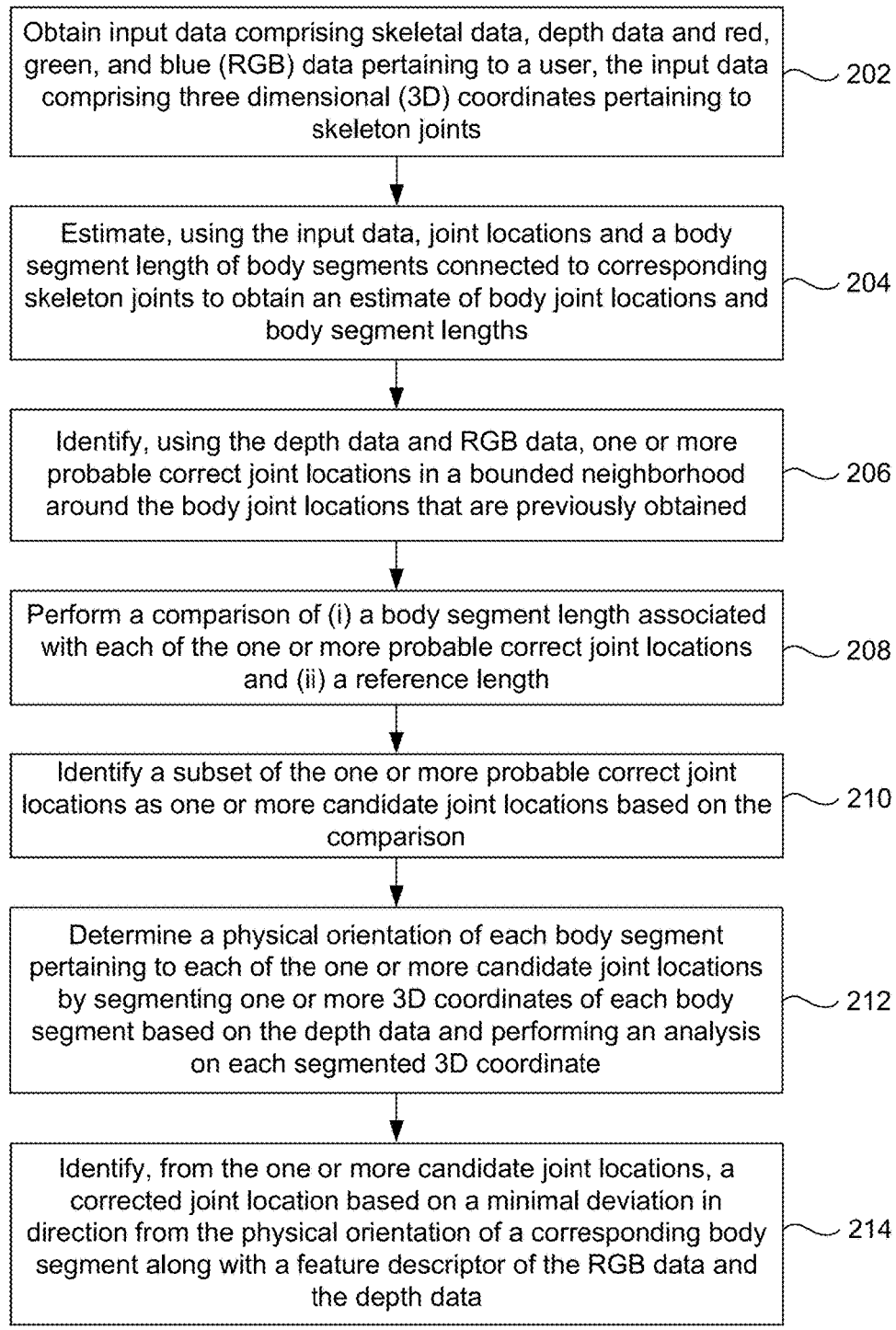
FIG. 2 illustrates an exemplary flow diagram of a method for identifying a body joint location of a user using the system of FIG. 1 in accordance with an embodiment of the present disclosure.

FIG. 2 illustrates an exemplary flow diagram of a method for identifying a body joint location of a user using the system 100 of FIG. 1 in accordance with an embodiment of the present disclosure. In an embodiment, the system 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIG. 1, and the flow diagram. In an embodiment of the present disclosure, at step 202, the one or more processors 104 obtain input data comprising skeletal data, depth data and red, green, and blue (RGB) data pertaining to at least one user. In an example embodiment, the input data may be captured at one or more time stamps. In an example embodiment, the one or more input data comprises three dimensional (3D) coordinates pertaining to one or more skeleton joints. In an example embodiment, the input data comprising skeletal data, depth data and red, green, and blue (RGB) data is captured by a sensor, for example, a Kinect® sensor. In an example embodiment, the skeletal data, depth data and red, green, and blue (RGB) data is received from the Kinect® sensor at a frame rate of approximately 25-30 frames per second The Kinect® sensor may be integrated within the system 100, in one example embodiment. The Kinect® sensor may be an external component that is connected to the system 100 via one or more communication interfaces, in another example embodiment.

In an embodiment of the present disclosure, at step 204, the one or more processors 104 estimate (or compute) one or more body joint locations and a body segment length of one or more body segments connected to corresponding skeleton joints to obtain (i) an estimate of one or more estimated body joint locations and (ii) an estimate of one or more estimated body segment lengths. In an embodiment, the one or more body segment lengths are based on a Euclidean distance between adjacent skeleton joints in the skeleton data input. In an example embodiment, the estimate of the body joint locations and the body segment lengths are obtained using the input data.

In an embodiment of the present disclosure, at step 206, the one or more processors 104 iteratively identify one or more probable correct body joint locations in a bounded neighborhood around the one or more body joint locations that are previously obtained from a previous frame. In one embodiment of the present disclosure, the one or more probable correct body joint locations are iteratively identified based on the depth data and the RGB data. In an example embodiment of the present disclosure, a search region is defined for identifying the one or more probable correct body joint locations using a radius equivalent to a displacement of a corresponding skeleton joint in a single frame. In an embodiment of the present disclosure, at step 208, the one or more processors 104 perform a comparison of (i) a body segment length associated with each of the one or more probable correct body joint locations and (ii) a reference length. In an example embodiment, the reference length is computed or derived based on the estimate of the one or more body segment lengths (e.g., true body segment lengths). In other words, the reference length is computed or derived based on Euclidean distance between body joint locations during system initialization. The initial estimates of the body joint locations (e.g., true body joint locations) and the reference length of body segment are computed by taking the average of input skeleton joint location and Euclidean distance between adjacent input joint locations respectively, after removing outliers, if any.

In an embodiment of the present disclosure, at step 210, the one or more processors 104 identify at least a subset of the one or more probable correct body joint locations as one or more candidate body joint locations based on the comparison. In an example of the present disclosure, the subset of the one or more probable correct body joint locations are identified as one or more candidate body joint locations based on the comparison resulting in a minimal body segment length variation. In other words, probable correct body joint locations having a minimal body segment length variation with respect to the reference length are identified as the one or more candidate body joint locations.

Figure 7:
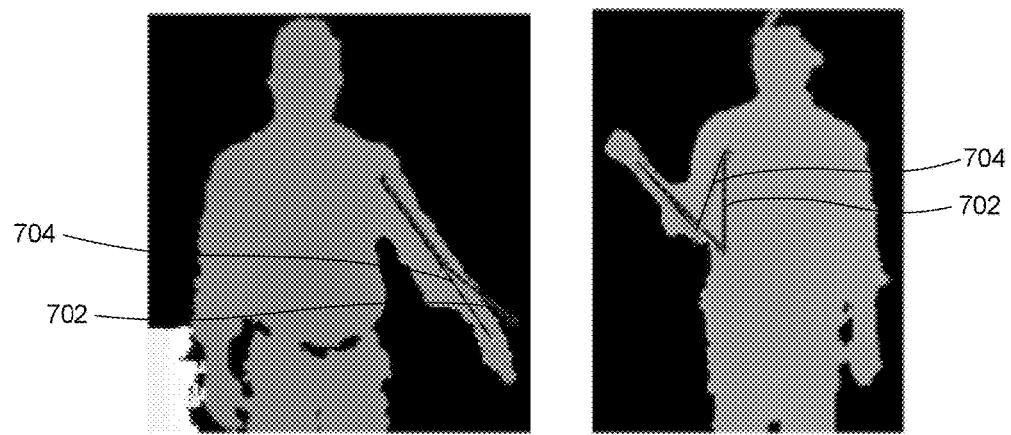
FIG. 7 depicts Body segment orientation correction by the system of FIG. 1 in accordance with an embodiment of the present disclosure.

In an embodiment of the present disclosure, at step 212, the one or more processors 104 determine a physical orientation of each body segment pertaining to each of the one or more candidate body joint locations by segmenting one or more 3D coordinates of each body segment based on the depth data and performing an analysis on each segmented 3D coordinate. In one embodiment of the present disclosure, the system 100 performs a principle component analysis on each segmented 3D coordinate, based on which the physical orientation is determined. In an embodiment of the present disclosure, at step 214, the one or more processors 104 identify a corrected body joint location from the one or more candidate body joint locations based on a deviation in direction from the physical orientation of a corresponding body segment along with a feature descriptor of the RGB data and the depth data, wherein the minimal deviation is based on the depth data. In an example embodiment of the present disclosure, the system 100 uses the RGB-D based feature descriptor to identify a corrected body joint location having (or that has) a minimal deviation in direction from the physical orientation of a corresponding body segment (as depicted in FIG. 7). In an embodiment, the minimal deviation is based on, or subject to, one or more actions performed by the user.

Experimental Setup

Ten healthy subjects (age: 21-65 years, weight: 45 kg-120 kg and height: 1:42 m-1:96 m) with no pre-existing symptoms of neurological diseases, major orthopedic lesions or vestibular disorders, were chosen for the experiments. The Kinect® v1 device has been used to capture Depth, RGB and Skeleton data (at 25 fps approximately) along with time-stamp information. Participants/subjects stood at a distance of 2:1 meters-2:4 meters from the Kinect® device (Kinect® sensor), which was placed 1 meter above the ground. Each participant performs the following (active) Range of motion (ROM) exercises—shoulder abduction and adduction, shoulder flexion and extension, elbow flexion and extension. In all experiments for an initial 1-2 seconds the subjects were required to stand completely stationary for initialization of the proposed methodology.

Joint movement analysis using Kinect® sensor is based on spatio-temporal variation of three-dimensional coordinates of 20 skeleton joints given by:

$$C_t = \{\vec{C}_t^j; j \in [1, 20]\}$$

Where $\vec{C}_t^j$ denotes the 3D coordinates of the $j^{th}$ joint provided by the Kinect® sensor at time instance t (corresponding to frame $f_t$). Let $\vec{B}_{ij}$ represent the body segment connecting joints i and j. The joint coordinates are subject to noise due to room lighting (or any other ambient affecting conditions), infrared (IR) interferences, subject's distance from Kinect® sensor, quantization errors introduced during computations etc. The errors in joint center locations $\vec{C}_t^j$ and $\vec{C}_t^i$ causes variation in length of $\vec{B}_{i,j}$, as well as its orientation in 3D space.

Hence, in order to reliably measure parameters such as joint range of motion, correct body joint locations are obtained that result in an accurate body segment length and orientation. With (direct) utilization of the depth sensor values as well as RGB information, it is possible to obtain the correct estimate of the joint's location that satisfies body segment length and orientation constraints. The intuition is that the correct location $\vec{C}_t^{*j}$ of the $j^{th}$ joint must lie in the vicinity of the 3-D coordinates $\vec{C}_t^j$ reported by the Kinect® sensor. A hierarchical searching technique is carried out, as described in the steps of FIG. 2, for the body joint location that satisfies—(1) maximum similarity in time-varying characteristics of depth and RGB, represented by a proposed feature descriptor, (2) maximum alignment of $\vec{B}_{i,j}$ towards true physical body segment orientation, (which is estimated from depth segmentation and analysis such as principle component analysis), and (3) minimum deviation in $\|B_{i,j}\|$ from reference length estimated during the initialization phase.

During the initialization phase when the subject(s) is made to remain stationary for 30-50 frames, an initial estimate of the body joint locations and the body segment length is computed based on quartile measures of observations. For each joint, candidate locations are searched in the vicinity of the Kinect® skeleton coordinates, which satisfy the constraint of minimal variation in length of body segment. Then the search is further refined by minimizing temporal variations in RGB-D based feature descriptor weighted by the deviation in direction of $\vec{B}_{i,j}$ from the physical orientation of the body segment.

Coordinate Transformation:

In order to find depth and RGB value for a particular joint j, the real world coordinates $\vec{C}_t^j = (X_t^j, Y_t^j, Z_t^j)^T$ are projected to two-dimensional depth map coordinates $\vec{P}_t^j = (px_t^j, py_t^j)^T$ using Kinect® IR camera intrinsic properties as shown in below expression (1) by way of example. Further an affine transformation is used to find correspondence between depth coordinates $\vec{P}_t^j$ and RGB image coordinates $\vec{R}_t^j = (rx_t^j, ry_t^j)^T$ as shown in below expression (2) by way of example:

$$f_1 = \vec{C} \in R^3 \to \vec{P} \in R^2 \qquad (1)$$

$$f_2 = \vec{P} \in R^2 \to \vec{R} \in R^2 \qquad (2)$$

Search for Body Joint Location:

The corrected body joint location $\vec{C}_t^{*j}$ at time t is searched in a bounded neighborhood around $\vec{C}_t^j$ in projected depth and RGB space (coordinate transformation as described above). The search region S for $j^{th}$ joint at the time t is defined using a radius equivalent to the joint's displacement in a single frame.

Body Segment Length Constraint:

The search is subject to the constraint that body segment length (the Euclidean distance between 3D coordinates of two physically connected joints) should remain invariant during movement of the corresponding joints. The search region S is refined to S1 by selecting candidate locations $\vec{Q}_t^j \in S$ that satisfy the length constraint, as shown in below expression by way of example:

$$S1 = \left\{ \vec{Q}_t^j \in S : \sum_i \left| L_t^{(i,j)} - \hat{L}^{(i,j)} \right| < \epsilon, \forall \text{ connected}(i,j), (\epsilon \to 0) \right\} \qquad (3)$$

Where $\vec{C}_t^{*i}$ is the corrected 3D location of joint i, $L_t^{(i,j)}$ is the Euclidean distance between $f_1^{-1}(\vec{Q}_t^j)$ and $\vec{C}_t^{*t}$. $\hat{L}^{(i,j)}$ is the physical length of the body segment joining joints i and j, which is estimated during initialization. In one example embodiment, the search regions S and S1 may be defined by the system 100. In another example embodiment, one or more inputs may be obtained (e.g., from a user) by the system to define the search regions S and S1.

Estimation of Body Segment Orientation:

At each time instance t, the vector $\vec{B}_{i,j}$ is selected so that it exhibits maximum alignment towards the true body segment orientation. It is possible to segment the human body from the background in Kinect® Depth space. A bounded region around the body joint location of joints i and j is used to separate the coordinates of the body segment or limb from the rest of the human (user) form. An analysis (e.g., but not limited to, principle component analysis) is performed over segmented coordinates to get an Eigen vector $\vec{E}_{i,j}$ whose direction represents the direction of maximum variation of coordinates representing the body segment. $\vec{E}_{i,j}$ provides an estimate of the physical orientation of the body orientation in each instance of time.

Feature Descriptor

The search region (or space) S1 consists of candidate locations among which the joint's actual location lies. In order to select the true body joint location (example, an exact or actual body joint location amongst the one or more candidate body joint locations), a set of features based on RGB and depth characteristics is used to uniquely identify the joint as it makes it's trajectory over time.

During any ROM exercise, in-spite of variation of depth values for any joint, the relative depth variation between a depth-pixel and its neighbors ought to remain unchanged for any two consecutive frames. The RGB values in a pixel neighborhood demonstrate similar properties. For a joint centre $\vec{C}_t^j = (X_t^j, Y_t^j, Z_t^j)^T$, feature descriptor consisting of elements related to depth differences and RGB values is defined as $\lambda = \{\lambda_D, \lambda_R\}$. $\lambda_D$ is a $(2w+1) \times (2w+1)$ matrix where $w \in I^+$ centered at depth pixel $\vec{P} = (px, py)^T$ and is expressed as $\lambda_D \in \vec{P}_t^j$. Hereafter the notation $\lambda_D \in \vec{Q}$ is used to denote $\lambda_D$ centered at any arbitrary location $\vec{Q}$.

$$\begin{bmatrix} D_{px-w, py-w} & \cdots & \cdots \\ \cdots & D_{px, py} & \cdots & \cdots \\ \cdots & \cdots & D_{px+w+1, py+w+1} \end{bmatrix} \qquad (4)$$

Where $D_{x,y} = (\text{depth}_{(px, py)} - \text{depth}_{(x, y)}) * g(x, y)$ depth$(x, y)$=depth value at coordinates $(x, y)$ g(x,y) represents a Gaussian window centered at $\vec{P}$ with variance $\sigma^2$.

Similarly $\lambda_R$ centered at $\vec{R}_t^j = (rx_t^j, ry_t^j)^T = f_2(\vec{P}_t^j)$ (for the same window) is expressed as $\lambda_R | \vec{P}_t^j$.

Finally the corrected location $\vec{C}_t^{*j}$ for joint j is obtained by the following equations:

$$\vec{C}_t^{*j} = f_1^{-1}(\vec{Q}_t^{*j})$$

$$\vec{Q}_t^{*j} = \underset{\vec{Q}_t^j \in S1}{\operatorname{argmin}}\left( \gamma \delta_1(\vec{Q}_t^j) \cdot \delta_2(\vec{Q}_t^j) \right)$$

$$\delta_1(\vec{Q}_t^j) = \alpha\left( \left\| \lambda_D | \vec{Q}_t^j - \lambda_D | \vec{P}_{t-1}^{*j} \right\| \right) + (1-\alpha)\left( \left\| \lambda_R | \vec{Q}_t^j - \lambda_R | \vec{P}_{t-1}^{*j} \right\| \right)$$

$$\delta_2(\vec{Q}_t^j) = \operatorname{direction}\left( \vec{C}_t^{*i} - \vec{Q}_t^j \right) - \operatorname{direction}(\vec{E}_{i,j})$$

where $\alpha, \gamma \in (0, 1)$ are constants, whose values may be experimentally determined.

FIG. 3, with respect to FIGS. 1-2, illustrates an exemplary table indicating body segment length statistics for ROM exercises for 10 subjects, according to an embodiment of the present disclosure. More particularly, FIG. 3 depicts correction and/or percentage (%) improvement in body segment length each ROM exercise with respect to mean (in meter), standard deviation (in meter), range (in meter), co-efficient of variation for input data obtained from a Kinect® sensor. As depicted in FIG. 3, for example, for Shoulder ROM exercise (Abduction Adduction), the percentage (%) improvement in body segment length is 73.8 and 74.3 respectively. Similarly, for Shoulder ROM exercise (Flexion and Extension), the percentage (%) improvement in body segment length is 72.9 and 80.7 respectively. Likewise, for Elbow ROM exercise (Flexion and Extension) the percentage (%) improvement in body segment length is 71.6 and 58.7 respectively.

Figure 4:
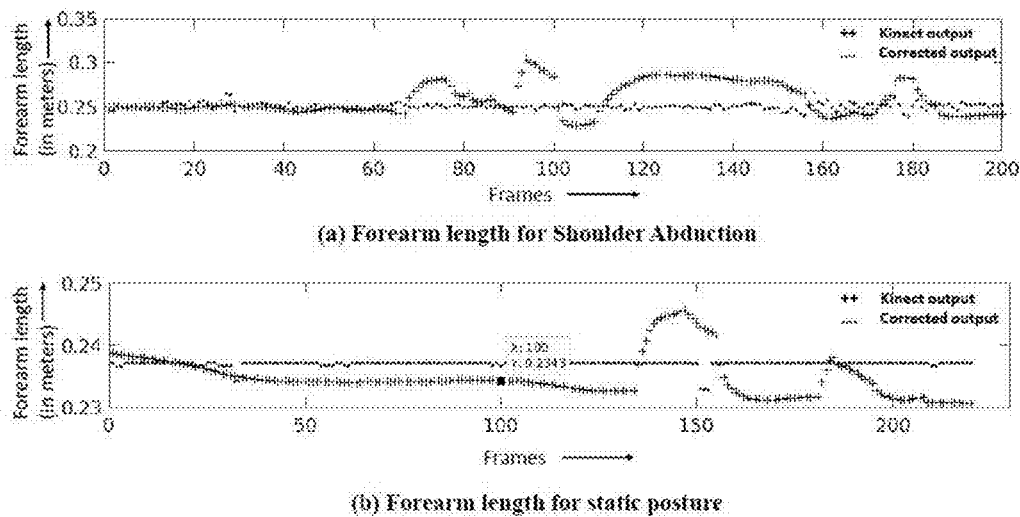
FIG. 4 illustrates a graphical representation of variation in length of forearm joints in accordance with an embodiment of the present disclosure.
Figure 5:
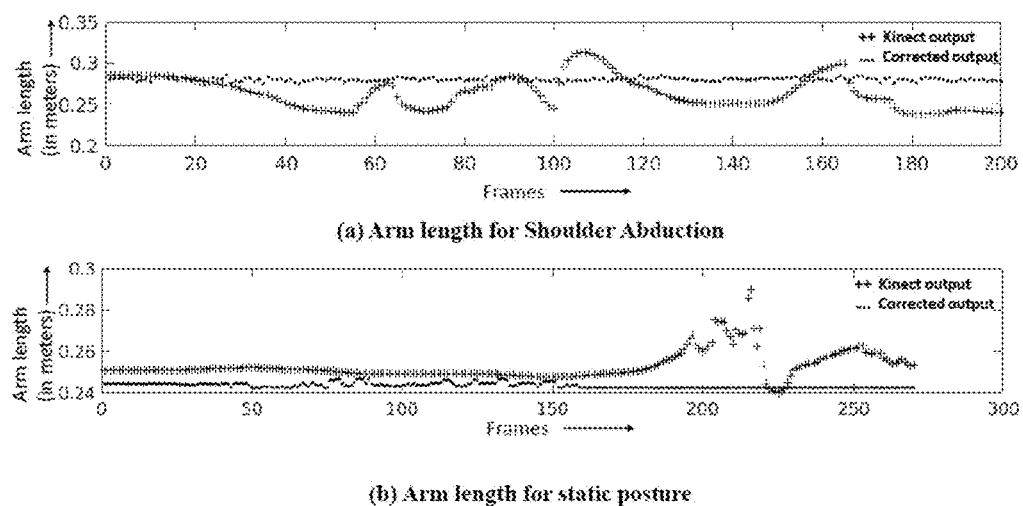
FIG. 5 illustrates a graphical representation of variation in length of arm in accordance with an embodiment of the present disclosure.

FIG. 4, with reference to FIGS. 1 through 3, illustrates a graphical representation of variation in length of forearm joints in accordance with an embodiment of the present disclosure. More specifically, FIG. 4 depicts variation in length between elbow left and wrist left joints. FIG. 5, with reference to FIGS. 1 through 4, illustrates a graphical representation of variation in length of arm in accordance with an embodiment of the present disclosure. More specifically, FIG. 5 depicts variation in length between shoulder left and elbow left joints. The performance is evaluated by the system 100 both for stationary and dynamic joints. FIGS. 4 and 5 indicate a significant reduction in temporal variation of arm and forearm length during shoulder abduction, with the proposed methodology.

Figure 6:
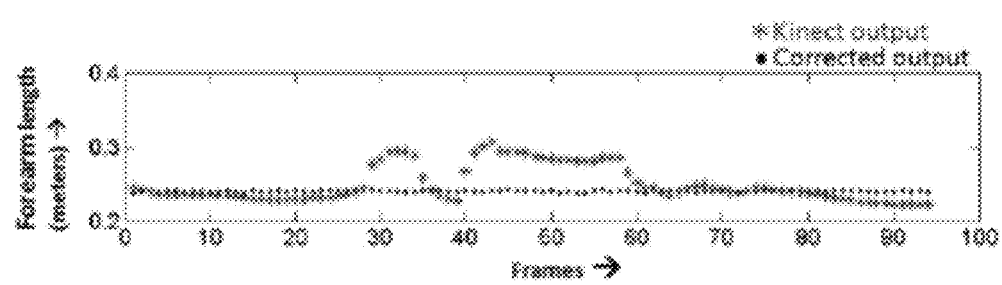
FIG. 6 illustrates a graphical representation of variation in forearm length for elbow flexion in accordance with an embodiment of the present disclosure.

FIG. 6, with reference to FIGS. 1 through 5, illustrates a graphical representation of variation in forearm length for elbow flexion in accordance with an embodiment of the present disclosure. FIG. 6 clearly shows similar trend for elbow flexion and extension. Performance comparison of length variation is carried out for all subjects using the following metrics—mean, standard deviation, range and coefficient of variation (CV) as depicted in the table of FIG. 3. The results reported in the table of FIG. 3 indicate a clear reduction in standard deviation of body segment length from the order of 1-2 centimeters for Kinect skeleton data to a few millimeters for corrected skeleton data. There is an average 72% improvement in CV over all ROM exercises and all subjects.

Body Segment Orientation Correction:

FIG. 7, with reference to FIGS. 1 through 6, depicts Body segment orientation correction by the system 100 of FIG. 1 in accordance with an embodiment of the present disclosure. More specifically, FIG. 7 depicts body segment orientation wherein dotted line denotes Kinect® output 702, solid line denotes correction 704 by the system 100. The corrected joint information not only helps achieve higher accuracy of measurements for joint Range of Motion analysis, but also aids in improving reliability of other assessment (e.g., clinical) of posture, gait, balance etc. from Kinect® skeleton information (or Kinect® Skeletal data). The body segment orientation obtained from raw Kinect® coordinates often suffers from inaccuracy during motion, an example of which is shown in FIG. 7 where the 2D projection of the elbow and wrist skeletal coordinates is shown to exceed physical boundaries of the hand while the hand is in motion. This situation has been frequently observed during Range of Motion activities of multiple subjects. By correcting the orientation and length of body segment it is evident that the accuracy of dynamic measurement of joint angles is much higher. During range of motion exercise the corrected length and orientation of the limb may reflect the actual trajectory of the physical limb. It has been validated by the ROM measurement with a clinical Goniometer. For shoulder abduction the deviation of angle computed from Kinect® skeleton data is in the order of 6.39 degrees±5.06 degrees which eventually corresponds to the fact reported by conventional systems and methods, whereas the proposed method is able to reduce the deviation by 1.88 degrees±1.1 degrees. The proposed body segment length and orientation correction also influences joint angle and range of motion analysis.

The systems and methods of the present disclosure provide techniques to improve accuracy of Kinect® skeletal joint coordinates for various applications (e.g., but are not limited to, rehabilitation). The Kinect® skeleton being a non-anthropometric model, there are body segment length and orientation variations over time. The proposed method implemented by the system 100 achieves and improves accuracy in estimation of body segment length as well as aligns the coordinates in the direction of the physical body segment that helps reconstruct the dynamic trajectory and angle of the body segment motion as accurately as possible. Although embodiments of the present disclosure describe body joint location identification in a 3D space, the embodiments/method may be implemented by the system 100 to identify body joint location in 2D space (or N-dimensions) as well.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method comprising:
   obtaining, by one or more hardware processors, one or more input data comprising skeletal data, depth data and red, green, and blue (RGB) data pertaining to at least one user at one or more time stamps, wherein said one or more input data comprises three dimensional (3D) coordinates pertaining to one or more skeleton joints;
   estimating, using said one or more input data, by said one or more hardware processors, in a first set of frames, one or more body joint locations and a body segment length of one or more body segments connected to corresponding skeleton joints to obtain (i) an estimate of one or more body joint locations and (ii) an estimate of one or more body segment lengths;
   iteratively identifying, by said one or more hardware processors, one or more probable correct body joint locations in a bounded neighborhood around said one or more body joint locations that are previously obtained, wherein said one or more probable correct body joint locations are iteratively identified based on said depth data and said RGB data;
   performing, by said one or more hardware processors, a comparison of (i) a body segment length associated with each of said one or more probable correct body joint locations and (ii) a reference length;
   identifying, by said one or more hardware processors, at least a subset of said one or more probable correct body joint locations as one or more candidate body joint locations based on said comparison;
   determining a physical orientation of each body segment pertaining to each of said one or more candidate body joint locations by segmenting one or more 3D coordinates of each body segment based on said depth data and performing an analysis on each segmented 3D coordinate; and
   identifying, from said one or more candidate body joint locations, a body joint location based on a minimal deviation in direction from said physical orientation of a corresponding body segment along with a feature descriptor of said RGB data and said depth data, wherein said minimal deviation is based on said depth data, and wherein said minimal deviation is based on one or more actions performed by said user.

2. The processor implemented method of claim 1, wherein identifying, by said one or more hardware processors, at least a subset of said one or more probable correct body joint locations as one or more candidate body joint locations is based on said comparison resulting in a minimal body segment length variation.

3. The processor implemented method of claim 1, wherein a search region is defined for identifying said one or more probable correct body joint locations using a radius equivalent to a displacement of a corresponding skeleton joint.

4. The processor implemented method of claim 1, wherein said estimate of said one or more body segment lengths is based on a Euclidean distance between adjacent skeleton joints.

5. The processor implemented method of claim 1, wherein said reference length is derived based on said estimate of said one or more body segment lengths.

6. A system comprising:
   a memory storing instructions;
   one or more communication interfaces; and
   one or more hardware processors coupled to said memory using said one or more communication interfaces, wherein said one or more hardware processors are configured by said instructions to:
   obtain one or more input data comprising skeletal data, depth data and red, green, and blue (RGB) data pertaining to at least one user at one or more time stamps, wherein said one or more input data comprising three dimensional (3D) coordinates pertaining to one or more skeleton joints,
   estimate, using said one or more input data, one or more body joint locations and a body segment length of one or more body segments connected to corresponding skeleton joints to obtain (i) an estimate of one or more body joint locations and (ii) an estimate of one or more body segment lengths,
   identify one or more probable correct body joint locations in a bounded neighborhood around said one or more body joint locations that are previously obtained, wherein said one or more probable correct body joint locations are iteratively identified based on said depth data and said RGB data,
   perform a comparison of (i) a body segment length associated with each of said one or more probable correct body joint locations and (ii) a reference length;
   identify at least a subset of said one or more probable correct body joint locations as one or more candidate body joint locations based on said comparison,
   determine a physical orientation of each body segment pertaining to each of said one or more candidate body joint locations by segmenting one or more 3D coordinates of each body segment based on said depth data and performing an analysis on each segmented 3D coordinate, and identify, from said one or more candidate body joint locations, a body joint location based on a minimal deviation in direction from said physical orientation of a corresponding body segment along with a feature descriptor of said RGB data and said depth data, wherein said minimal deviation is based on said depth data, and wherein said minimal deviation is based on one or more actions performed by said user.

7. The system of claim 6, wherein at least a subset of said one or more probable correct body joint locations are identified as one or more candidate body joint locations based on said comparison resulting in a minimal body segment length variation.

8. The system of claim 6, wherein a search region is defined for identifying said one or more probable correct body joint locations based on a radius equivalent to a displacement of a corresponding skeleton joint.

9. The system of claim 6, wherein said estimate of said one or more body segment lengths is based on a Euclidean distance between adjacent skeleton joints.

10. The system of claim 6, wherein said reference length is derived based on said estimate of said one or more estimated body segment lengths.

11. One or more non-transitory machine readable information storage mediums comprising one or more instructions which when executed by one or more hardware processors causes:

obtaining, by one or more hardware processors, one or more input data comprising skeletal data, depth data and red, green, and blue (RGB) data pertaining to at least one user at one or more time stamps, wherein said one or more input data comprises three dimensional (3D) coordinates pertaining to one or more skeleton joints;

estimating, using said one or more input data, by said one or more hardware processors, in a first set of frames, one or more body joint locations and a body segment length of one or more body segments connected to corresponding skeleton joints to obtain (i) an estimate of one or more body joint locations and (ii) an estimate of one or more body segment lengths;

iteratively identifying, by said one or more hardware processors, one or more probable correct body joint locations in a bounded neighborhood around said one or more body joint locations that are previously obtained, wherein said one or more probable correct body joint locations are iteratively identified based on said depth data and said RGB data;

performing, by said one or more hardware processors, a comparison of (i) a body segment length associated with each of said one or more probable correct body joint locations and (ii) a reference length;

identifying, by said one or more hardware processors, at least a subset of said one or more probable correct body joint locations as one or more candidate body joint locations based on said comparison;

determining a physical orientation of each body segment pertaining to each of said one or more candidate body joint locations by segmenting one or more 3D coordinates of each body segment based on said depth data and performing an analysis on each segmented 3D coordinate; and identifying, from said one or more candidate body joint locations, a body joint location based on a minimal deviation in direction from said physical orientation of a corresponding body segment along with a feature descriptor of said RGB data and said depth data, wherein said minimal deviation is based on said depth data, and wherein said minimal deviation is based on one or more actions performed by said user.

12. The one or more non-transitory machine readable information storage mediums of claim 11, wherein identifying, by said one or more hardware processors, at least a subset of said one or more probable correct body joint locations as one or more candidate body joint locations is based on said comparison resulting in a minimal body segment length variation.

13. The one or more non-transitory machine readable information storage mediums of claim 11, wherein a search region is defined for identifying said one or more probable correct body joint locations using a radius equivalent to a displacement of a corresponding skeleton joint.

14. The one or more non-transitory machine readable information storage mediums of claim 11, wherein said estimate of said one or more body segment lengths is based on a Euclidean distance between adjacent skeleton joints.

15. The one or more non-transitory machine readable information storage mediums of claim 11, wherein said reference length is derived based on said estimate of said one or more body segment lengths.

* * * * *